United States Patent [19]

Huppatz

[11] 4,134,987

[45] Jan. 16, 1979

[54] COMPOUNDS AND COMPOSITIONS

[76] Inventor: John L. Huppatz, 15 Schumack St., Weetan gera, Australian Capital Territory, Australia

[21] Appl. No.: 756,069

[22] Filed: Jan. 3, 1977

[30] Foreign Application Priority Data

Jan. 14, 1976 [AU] Australia .............................. 4527/76

[51] Int. Cl.² ............................................... A01N 9/22
[52] U.S. Cl. .................. 424/273 P; 548/377; 548/378
[58] Field of Search ........................ 424/273, 273 P; 548/377, 378

[56] References Cited

U.S. PATENT DOCUMENTS

| | | | |
|---|---|---|---|
| 3,905,997 | 9/1975 | Zinnes et al. | 424/273 P |
| 3,931,406 | 1/1976 | Berenson | 424/273 |
| 3,953,467 | 4/1976 | Fujimura et al. | 424/273 P |
| 4,025,530 | 5/1977 | Crovetti et al. | 548/377 |

FOREIGN PATENT DOCUMENTS

| | | | |
|---|---|---|---|
| 2304584 | 8/1973 | Fed. Rep. of Germany | 548/378 |
| 49-116061 | 11/1974 | Japan | 424/273 P |
| 542149 | 12/1941 | United Kingdom. | |
| 1444678 | 8/1976 | United Kingdom. | |

OTHER PUBLICATIONS

C.A., vol. 20, 1926, pp. 2856-2857 Rojahn et al.

*Primary Examiner*—Allen J. Robinson
*Attorney, Agent, or Firm*—Cushman, Darby & Cushman

[57] ABSTRACT

Fungicidal compositions comprising as an active ingredient a compound of the general formula I

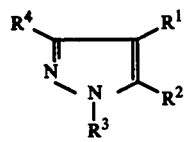

wherein either $R^1$ or $R^2$ is the group

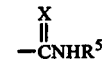

in which X is an oxygen atom or a sulphur atom and $R^5$ is straight chain alkyl group of 1 to 8 carbon atoms, branched chain alkyl group of 1 to 8 carbon atoms, cyclic alkyl group of 3 to 8 carbon atoms, alkenyl group, alkynyl group, hydroxyalkyl group phenyl group or a mono-, di- or tri- substituted phenyl group with substituents, which may be the same or different, chosen from the group consisting hydrogen alkyl, alkenyl, alkynyl, hydroxyalkyl, alkoxy, phenyl, halogen, trifluoromethyl, thiocyanate, nitro, cyano, amino, carboxy, alkoxycarbonyl, carbamoyl, N-alkylcarbamoyl and N,N-dialkylcarbamoyl; when $R^1$ is the group

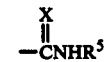

then $R^3$ is hydrogen, alkyl, alkenyl alkynyl, hydroxyalkyl, phenyl, $CH_2CF_3$ or the group $—CH_2COOR^6$ wherein $R^6$ is alkyl, phenyl or substituted phenyl, and $R^2$ and $R^4$, which may be the same or different, are hydrogen, alkyl, alkenyl, alkynyl, hydroxalkyl, alkoxy, phenyl, halogen, trifluoromethyl, thiocyanate, nitro, cyano, amino, carboxy, alkoxycarbonyl, carbamoyl, N,alkylcarbamoyl, N,N-dialkylcarbamoyl, hydroxy or mercapto provided that $R^2$ and $R^4$ are not both hydrogen, hydroxy or mercapto; when $R^2$ is the group

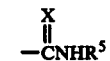

then $R^3$ is hydrogen, alkyl, alkenyl, alkynyl, hydroxyalkyl, phenyl or substituted phenyl, and $R^1$ and $R^4$, which may be the same or different, are hydrogen, alkyl, alkenyl, hydroxyalkyl, alkoxy, phenyl, substituted phenyl, halogen, trifluoromethyl, thiocyanate, nitro, cyano, amino, carboxy, alkoxycarbonyl, carbamoyl, N-alkylcarbamoyl, N,N-dialkylcarbamoyl, hydroxy or mercapto, provided that $R^1$ and $R^3$ are not both hydrogen and provided that $R^1$ and $R^4$ are not both hydroxy or mercapto; and an inert carrier material therefor.

16 Claims, No Drawings

COMPOUNDS AND COMPOSITIONS

This invention relates to new fungicidal compositions containing pyrazole derivatives as an active ingredient and to methods of combatting plant fungal diseases using them.

Accordingly the present invention provides fungicidal compositions comprising as an active ingredient a compound of the general formula I

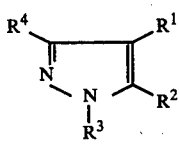

wherein either $R^1$ or $R^2$ is the group

in which X is an oxygen atom or a sulphur atom and $R^5$ is straight chain alkyl group of 1 to 8 carbon atoms, branched chain alkyl group of 1 to 8 carbon atoms, cyclic alkyl group of 3 to 8 carbon atoms, alkenyl group, alkynyl group, hydroxyalkyl group, phenyl group or a mono-, di- or tri- substituted phenyl group with subsituents, which may be the same or different, chosen from the group comprising hydrogen, alkyl, alkenyl, alkynyl, hydroxyalkyl, alkoxy, phenyl, halogen, trifluoromethyl, thiocyanate, thicyanate, nitro, cyano, amino, carboxy, alkoxycarbonyl, carbamoyl, N-alkylcarbamoyl and N,N-dialkylacarbamoyl; when R' is the group

then $R^3$ is hydrogen, alkyl, alkenyl, alkynyl, hydroxyalkyl, phenyl, $CH_2CF_3$ or the group $—CH_2COOR^6$ wherein $R^6$ is alkyl, phenyl or substituted phenyl, and $R^2$ and $R^4$, which may be the same or different, are hydrogen, alkyl, alkenyl, alkynyl, hydroxalkyl, alkoxy, phenyl, substituted phenyl, halogen, trifluoromethyl, thiocyanate, nitro, cyano, amino, carboxy, alkoxycarbonyl, carbamoyl, N-alkylcarbamoyl, N,N-dialkylcarbamoyl, hydroxy or mercapto provided that $R^2$ and $R^4$ are not both hydrogen, hydroxy or mercapto; when $R^2$ is the group

then $R^3$ is hydrogen, alkyl, alkenyl, alkynyl, hydroxyalkyl, phenyl or substituted phenyl, $R^1$ and $R^4$, which may be the same or different, are hydrogen, alkyl, alkenyl, hyroxyalkyl, alkoxy, phenyl, substituted phenyl, halogen, trifluoromethyl, thiocyanate, nitro, cyano, amino, carboxy, alkoxycarbonyl, carbamoyl, N-alkylcarbamoyl, N,N-dialkylcarbamoyl, hydroxy or mercapto, provided that $R^1$ and $R^3$ are not both hydrogen and provided that $R^1$ and $R^4$ are not both hydroxy or mercapto; and an inert carrier material therefor.

Unless otherwise stated, by alkyl, alkenyl, alkynyl and hydroxyalkyl we mean a group containing from 1 to 4 carbon atoms.

It is to be understood that when either $R^2$ or $R^4$ is a hydroxy or mercapto group the compounds of the invention may exist in a tautomeric form of the general formula II or III respectively,

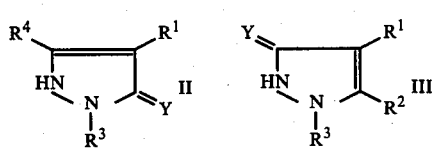

wherein Y is an oxygen atom or a sulphur atom and $R^1$, $R^2$, $R^3$ and $R^4$ are as defined hereinabove.

Preferred fungicidal compositions of the present invention comprise as an active ingredient a compound of the general formula I wherein $R^3$ is hydrogen, alkyl, phenyl, or substituted phenyl; $R^4$ is alkyl; and $R^2$ is hydrogen, alkyl or halogen when $R^1$ is the group $—CONHR^5$ and $R^1$ is hydrogen or alkyl when $R^2$ is the group $—CONHR^5$, wherein $R^5$ is phenyl or a mono-, di- or trisubstituted phenyl group. Specific compounds useful as active ingredients in the pesticidal compositions of this invention are listed in Tables I, II, III and IV below.

TABLE I

Compounds of General Formula IV:

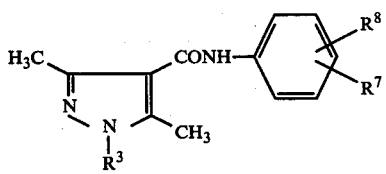

| Compound No | $R^3$ | $R^7$ | $R^8$ | Physical Characteristic M.p.(° C) |
|---|---|---|---|---|
| 1 | $CH_2CH_2OH$ | H | H | 162–4 |
| 2 | $CH_2COOCH_2CH_3$ | H | H | 172–4 |
| 3 | H | H | H | 244–5 |
| 4 | H | 2-$CH_3$ | H | 230–2 |
| 5 | H | 3-$CH_3$ | H | 209–11 |
| 6 | H | 3-Cl | H | 234–5 |
| 7 | H | 4-Cl | H | 271–2 |
| 8 | H | 3-Cl | 4-Cl | 259–60 |
| 9 | H | 4-$OCH_2CH_3$ | H | 234–5 |
| 10 | H | 2-$NO_2$ | H | 224–5 |
| 11 | $CH_3$ | H | H | 161–3 |
| 12 | $CH_3$ | 2-$CH_3$ | H | 152–3 |
| 13 | $CH_3$ | 3-$CH_3$ | H | 159–61 |
| 14 | $CH_3$ | 3-Cl | H | 155–6 |
| 15 | $CH_3$ | 4-Cl | H | 206–7 |
| 16 | $CH_3$ | 3-Cl | 4-Cl | 168–70 |
| 17 | $CH_3$ | 4-$OCH_2CH_3$ | H | 163–4 |
| 18 | $CH_3$ | 2-$NO_2$ | H | 168–70 |
| 19 | $CH_3$ | 3-$CF_3$ | H | 112–4 |
| 20 | Phenyl | H | H | 182–3 |
| 21 | Phenyl | 2-$CH_3$ | H | 144–6 |
| 22 | Phenyl | 3-$CH_3$ | H | 148–9 |
| 23 | Phenyl | 3-Cl | H | 143–5 |
| 24 | Phenyl | 4-Cl | H | 218–9 |
| 25 | Phenyl | 3-Cl | 4-Cl | 212–3 |
| 26 | Phenyl | 4-$OCH_2CH_3$ | H | 193–4 |
| 27 | Phenyl | 2-$NO_2$ | H | 141–2 |

TABLE II

| Compound No | Structural Formula | Physical Characteristic M.p.(° C) |
|---|---|---|
| 28 | 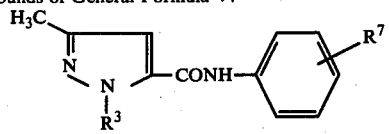 | 185-6 |

TABLE III

Compounds of General Formula V:

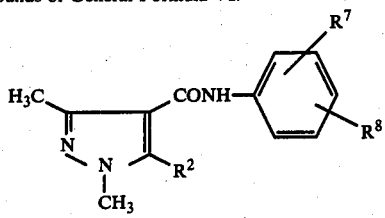

| Compound No | $R^3$ | $R^7$ | Physical Characteristic M.p. (° C) |
|---|---|---|---|
| 29 | $CH_3$ | H | 96-7 |
| 30 | $CH_3$ | 2-$CH_3$ | 158-60 |
| 31 | $CH_3$ | 3-$CH_3$ | 83-5 |
| 32 | $CH_3$ | 3-Cl | 115-7 |

TABLE IV

Compounds of General Formula VI:

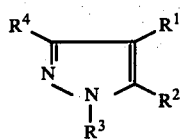

| Compound No | $R^2$ | $R^7$ | $R^8$ | Physical Characteristic M.p.(° C) |
|---|---|---|---|---|
| 33 | Cl | H | H | 157-159 |
| 34 | Cl | 3-Cl | H | 161-162 |
| 35 | H | H | H | 91-92 |

All of the compounds in Tables I, II, III and IV are new compounds with the exception of Compound 11 of Table I. Accordingly in a further aspect of our invention we provide new compounds of the general formula I

I wherein $R^1$, $R^2$, $R^3$ and $R^4$ have any of the meanings as defined hereinbefore except that $R^2$, $R^3$ and $R^4$ may not be methyl when $R^1$ is the group —CONHPh.

The actual compounds set out in Tables I, II, III and IV of this specification are well-defined crystalline solids having accurately determinable melting points.

The active compounds of our invention defined by the general formula I wherein $R^1$ is the group

may be prepared by one of the three following methods:

(a) bringing into reaction the appropriate 1,3-diketone (VII) and an isocyanate or isothiocyanate (VIII) and treating the resulting 2-carbamoyl-1,3-diketone (or 2-thiocarbamoyl-1, 3-diketone) (IX) with hydrazine or an appropriate monosubstituted hydrazine (X);

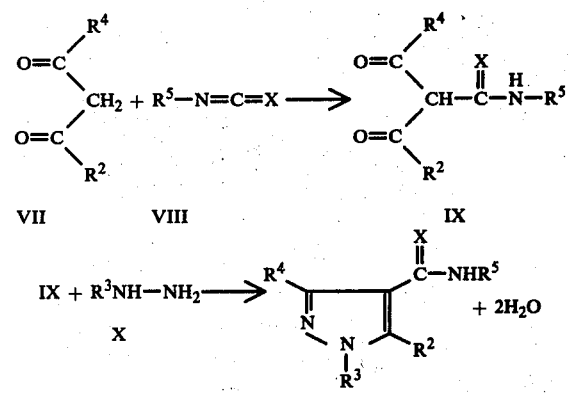

(b) bringing into reaction with appropriate 2-alkoxycarbonyl-1,3-diketone (XI) hydrazine or monosubstituted hydrazine (X), hydrolysing the resulting ester (XII) to the corresponding acid (XIII) and derivatizing the acid (XIII) by methods well known to those skilled in the art;

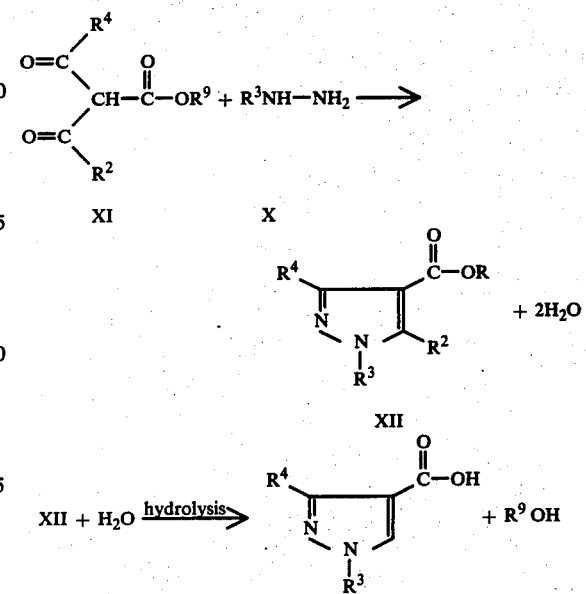

(c) bringing into reaction the appropriate α-keto carboxylic acid ester (XIV) and a monosubstituted hydrazine (X), treating the resulting pyrazolone (XV) with the appropriate isocyanate or isothiocyanate (VIII) and aromatising the resulting carboxamidopyrazolone (XVI) using, for example, phosphorous oxychloride.

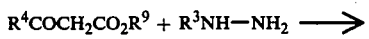

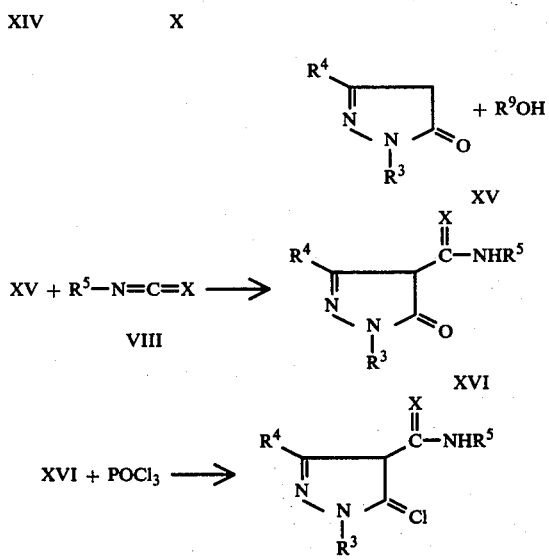

The active compounds of our invention defined by the general formula I wherein $R^2$ is the group

may be prepared by treating the appropriate 1,3-diketocarboxylic acid ester (XVII) with hydrazine or the appropriately monosubstituted hydrazine (X), hydrolysing the resulting ester (XVIII) to the corresponding acid (XIX), and derivatizing the acid (XIX) by methods well known to those skilled in the art.

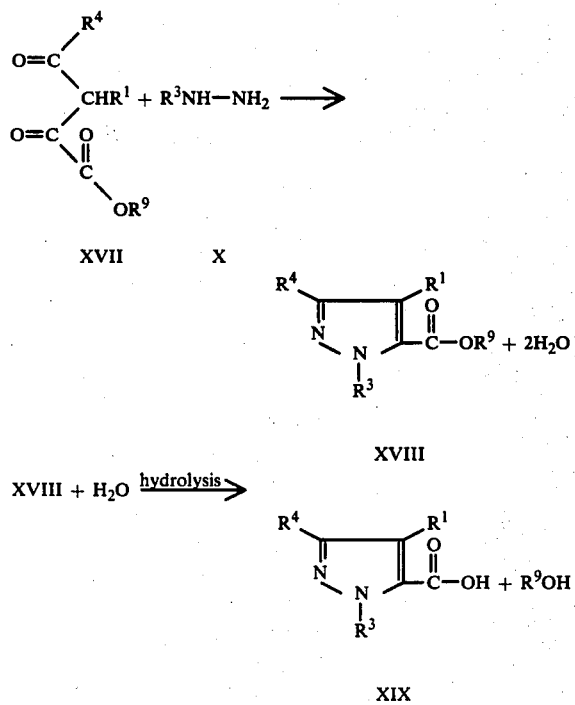

Accordingly, the invention also provides processes for the preparation of compounds of general formula I as hereinbefore defined.

The compositions and compounds of this invention are useful in combatting various of the following list of fungal diseases:

*Septoria nodorum;* (glume blotch)
  *Uromyces viciae-fabae;* (bean rust)
  *Cladosporium cucumerinum;* (gamosis)
  *Puccinia recondita;* (rust on wheat)
  *Rhizoctonia solani;* (root rot)
  *Phytophthora infestans;* (late blight on potato and tomato)
  *Xanthomonas oryzae;* (bacterial blight of rice)
  *Piriculania oryzae;* (blast on rice)
  *Ustilago nuda;* (loose smut)
  *Tilletia foetida;* (wheat bunt)
  *Monolinia fructicola;* (brown rot)
  *Phytophthora cinnamomi;* (cinnamon root rot)
  *Gauemannomyces graminis;* (take all)

Compound Nos 13, 14 of Table I and 33 of Table IV are particularly active against *Tilletia spp.*, Compound Nos 11, 12, 13 of Table I and 33 of Table IV are particularly useful against *Rhizoctonia solani,* Compound Nos 11, 14 and 17 of Table I are particularly active against *Uromyces viciae-fabae* and Compound Nos 13 of Table I is also useful against *Ustilago nuda* and *Puccinia recondita.*

A particularly useful feature of the activity of compounds of the present invention is their ability to move in a plant to combat an infection or infestation thereon remote from a site of initial application of a compound. Thus a compound of the invention, or a composition containing the same, may be applied to the soil surrounding the roots of a plant and taken up by the plant through its roots to combat pests on the plant.

In this respect Compound Nos 12 and 13 are especially useful as agents to combat the disease *Rhizoctonia solani.*

In use, the compositions or compounds of the invention may be applied in a number of ways. Thus their application can suitably be directly onto the foilage of the plants or to infected and/or infested areas thereof; alternately the soil surrounding the plant, or the stem of the plant, or soil in which seeds or plants are to be sown or planted is treated with the compositions or compounds of the invention. If desired, the seeds themselves can be similarly treated.

According to a further feature of the invention, therefore, we provide a process of combatting undesired fungal infestations in plants which process comprises applying to said plants or to the locus of said plants a fungicidally effective amount of a composition or compound of the invention.

The invention further includes a method of combatting fungal or insect infestations in plants which comprises applying to plant seeds a composition or compound of the invention.

In yet a further aspect of the invention, therefore, we provide a process of treating seeds which process comprises treating said seeds prior to sowing with a fungicidally effective amount of a composition or compound of the invention.

The compositions and compounds of the invention are useful for agricultural or horticultural purposes and the compound or type of composition used in any instance will depend upon the particular purpose for which it is to be used.

Compositions comprising the invention compounds may be in the form of dusting powders or granules wherein the active ingredient is mixed with a solid diluent or carrier. Suitable solid diluents or carriers may be, for example, keolinite (china clay) montmorillonite, attapulgite, talc, pumice, silica, calcium carbonate, gypsum, powdered magnesia, Fuller's earth, Hewitt's earth and diatomaceous earth. Compositions for dressing seed, for example, may comprise an agent assisting the adhesion of the composition to the seed, for example, a mineral oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic, or non-ionic type. Suitable agents of the cationic type include, for example, quaternary ammonium compounds, for example, cetyltrimethylammonium bromide. Suitable agents of the anionic type include, for example, soaps, salts or aliphatic monoesters of sulphuric acid, for example sodium lauryl sulphate, salts of sulphonated aromatic compounds, for example sodium dodecylbenzene sulphonate, sodium, calcium, or ammonium lignosulphonate, butylnaphthalene sulphonate, and a mixture of the sodium salts of diisopropyl- and triisopropylnaphthalene sulphonic acids.

Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other nonionic agents are the partial esters derived from long chain fatty acids and hexitol anhydrides, the condensation products of the said partial esters with ethylene oxide, the lecithins, and block copolymers of ethylene oxide and propylene oxide.

Suitable suspending agents are, for example, bentonite, pyrogenic silica, and hydrophilic colloids, for example polyvinylpyrrolidone and sodium carboxymethyl-cellulose, and the vegetable gums, for example gum acacia and gum tragancanth.

The aqueous solutions, dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, propylene glycol, diacetone alcohol, toluene, kerosene, methyl-naphthalene, xylenes and trichloroethylene.

The compounds of the invention may also be formulated into compositions comprising capsules or microcapsules containing either the active ingredient itself, or a composition containing the active ingredient, and prepared by any of the known encapsulation or microencapsulation techniques.

The compositions to be used as sprays may also be in the form of aerosols wherein the formulation is held in a container under pressure in the presence of a propellant such as fluorotrichlormethane or dichlordifluoromethane.

By the inclusion of suitable additives, for example, for improving the distribution, adhesive power and resistance to rain on treated surfaces, the different compositions can be better adapted for the various uses for which they are intended.

The compounds of this invention may also be conveniently formulated by admixing them with fertilizers. A preferred composition of this type comprises granules of fertilizer material incorporating, for example coated with, a compound of the invention. The fertilizer material may, for example, comprise nitrogen or phosphate-containing substances.

In yet a further aspect of the invention, therefore, we provide a fertilizer comprising a compound of the invention as hereinbefore defined.

The compositions which are to be used in the form of aqueous dispersions or emulsions are generally supplied in the form of a concentrate containing a high proportion of the active ingredient or ingredients, the said concentrate to be diluted with water before use.

These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10–85% by weight of the active ingredient or ingredients and generally from 25–60% by weight of the active ingredient or ingredients. When diluted to form aqueous preparations, such preparations may contain varying amounts of the active ingredient or ingredients depending upon the purpose for which they are to be used, but an aqueous preparation containing between 0.0001% and 1.0% by weight of active ingredient or ingredients may be used.

It is to be understood that the pesticidal compositions of this invention may comprise, in addition to a compound of the invention, one or more other compounds having biological activity.

Our invention is illustrated by, but by no means limited to, the following examples.

EXAMPLE 1

This example illustrates a method for the preparation of 3,5-dimethyl-N-phenyl-4-pyrazolecarboxamide (Compound No 3 of Table I).

A mixture of acetylacetone (5 g) and triethylamine (5.2 g) in dry benzene (50 ml) was treated with phenyl isocyanate (6 g) in dry benzene (25 ml). The mixture was stirred for 3 hr at room temperature. Water (50 ml) was then added, the mixture shaken and the water layer separated. The benzene solution was extracted with two further portions (25 ml) of water and the combined aqueous extracts acidified with dilute hydrochloric acid. The product precipitated and was collected by filtration, washed with water and dried. Diacetyl acetanilide (7.0 g, 73%) was obtained as a colourless solid, m.p. 119–121° C.

The foregoing diacetyl acetanilide (2.2 g) in glacial acetic acid (30 ml) was treated with hydrazine hydrate (1.5 g) and the mixture boiled under reflux for 30 min. The mixture was then poured into water and the product collected and crystallised from ethanol. 3,5-dimethyl-N-phenyl-4-pyrazolecarboxamide (1.9 g, 86%) was obtained as colourless plates, m.p. 244–5° C (Found: C, 66.8 H, 6.0 N, 19.3 $C_{12}H_{13}N_3O$ requires C, 66.9; H, 6.1; N, 19.5%).

EXAMPLE 2

This example illustrates a method for the preparation of N-cyclohexyl-1,3,5-trimethyl-4-pyrazolecarboxamide (Compound No 28 of Table II).

Ethyl diacetylacetate (Organic Syntheses, Coll. Vol. 3, 1955, p. 309) (51.6 g) in ethanol (200 ml) was treated with methyl hydrazine (15 g) in portions. The mixture was then refluxed gently for 1 hr. About half the ethanol was then removed in vacuo and the residue poured into 5% NaCl solution (300 ml). The product was extracted with chloroform and the chloroform extracts dried and evaporated. The crude 1,3,5-trimethyl-4-ethoxycarbonylpyrazole was hydrolysed with aqueous ethanolic sodium hydroxide solution. The acid (85%) was purified by crystallisation from water; it had m.p. 222–3° C (Rojahn and Kuhling, Archiv. der Pharmazie (1926), 341; Chem Abs. 20, 2857 (1926), give m.p. 217° C for this compound).

The 1,3,5-trimethyl-4-carboxypyrazole above (3.1 g) was added to thionyl chloride (10 ml) and the mixture heated on a steam-bath under reflux and protected from moisture for 1 hr. After removal of the excess thionyl chloride, cyclohexylamine (2.5 g) in pyridine (20 ml) was added and the mixture heated on the steam-bath a further 1 hr. The mixture was then poured into 5% hydrochloric acid and the product collected. Crystallisation from aqueous ethanol gave 1, N-cyclohexyl-1,3,5-trimethyl-4-pyrazolecarboxamide (75% yield), m.p. 185–6° C.

EXAMPLE 3

By adopting the appropriate procedures and methods similar to those described in Examples 1 and 2 above, and using the appropriate reactants the specific compounds set out in Table I (excluding that prepared in Example 1) were prepared.

EXAMPLE 4

This example illustrates a method for the preparation of 1,3-dimethyl-N-(o-tolyl)5-pyrazolecarboxamide (Compound No 30 of Table III).

Ethyl acetopyruvate (Organic Syntheses, Coll. Vol. I, 1944, p. 238) (31.6 g) was dissolved in ethanol (100 ml) and treated with methyl hydrazine (12 g) in portions. The mixture was then refluxed gently for 1 hr, whereupon most of the ethanol was removed in vacuo. The residue was poured into 5% NaCl solution and the product extracted with chloroform (3 × 100 ml). The combined extracts were washed with water, dried and the solvent evaporated. The residue was then distilled in vacuo. 1,3-dimethyl-5-ethoxycarbonylpyrazole (14.5 g 43%) was obtained as a colourless oil, b.p.$_{25}$ 118–121° C. (A mixture of the two isomers (1.5 g), followed by pure 1,5-dimethyl-3-ethoxycarbonylpyrazole (10.5 g, 31%), b.p.$_{25}$ 178–180° C, was obtained on continued distillation).

The foregoing 1,3-dimethyl-5-ethoxycarbonylpyrazole (14 g) was hydrolysed with aqueous ethanolic sodium hydroxide. The corresponding acid (10.8 g, 93%) was obtained as a colourless solid m.p. 207–9° C (Elguero et al., Bull. Soc. Chim. France (1966), 293; Chem. Abs. 64, 15866(1966), give m.p. 207° C for this compound). The acid (3.5 g) was converted to the acid chloride by heating with thionyl chloride. After removal of excess thionyl chloride in vacuo, the crude acid chloride was treated with a mixture of o-toluidine (3 g) in pyridine (20 ml). The mixture was heated on a steam-bath for 1 hr, and then poured into 5% hydrochloric acid (200 ml). The product was filtered and crystallised from aqueous ethanol. 1,3-dimethyl-N-(o-tolyl)-5-pyrazolecarboxamide (4.9 g, 88%) was obtained as colourless needles, m.p. 158–160° C (Found: C, 68.0; H, 6.6; N, 18.1 $C_{13}H_{15}N_3O$ requires: C, 68.1; H, 6.6; N, 18.3%).

EXAMPLE 5

By adopting the appropriate procedures and methods similar to that described in Example 4 above, and using the appropriate reactants, the specific compounds set out in Table III (excluding that prepared in Example 4) were prepared.

EXAMPLE 6

This example illustrates methods for the preparation of 5-chloro-1,3-dimethyl-N-phenyl-4-pyrazolecarboxamide 5-chloro-N-(3-chlorophenyl)-1,3-dimethyl-4-pyrazolecarboxamide 1,3-dimethyl-N-phenyl-4-pyrazolecarboxamide (Compounds 33, 34 and 35 respectively, of Table IV).

(a) 1,3-Dimethylpyrazol-5-one

Methyl hydrazine (25 g) was added in portions to a solution of ethyl acetoacetate (65 g) in ethanol (250 ml). The mixture was refluxed gently for 1 hr, whereupon the ethanol was removed in vacuo. The residue was crystallised from benzene and 1,3-dimethylpyrazole-5-one (52 g, 93%) was obtained as colourless cubic crystals, m.p. 117–119° C. (lit. m.p. 117° C; Beilstein, Vol. 24, p. 19).

(b) 4,5-dihydro-1,3-dimethyl-5-oxo-N-phenyl-4-pyrazolecarboxamide 1,3-Dimethylpyrazole-5-one above (11.2 g) and triethylamine (10.2 g) were dissolved in dry benzene and phenyl isocyanate (12 g) added. The mixture was stirred 16–18 hrs at room temperature, whereupon it was extracted with water (4 × 50 ml). The combined aqueous extracts were acidified with dilute hydrochloric acid and the mixture refrigerated for several hours. The product was then recovered by filtration and dried. 4,5-dihydro-1,3-dimethyl-5-oxo-N-phenyl-4-pyrazolecarboxamide (17.5 g, 76%) was obtained as a colourless powder, m.p. 231–233° C.

From 3-chlorophenyl isocyanate, -N-(3-chlorophenyl)-4,5-dihydro-1,3-dimethyl-5-oxo-4-pyrazolecarboxamide was similarly obtained in 80% yield, m.p. 242–243° C.

(c) 5-chloro-1,3-dimethyl-N-phenyl-4-pyrazolecarboxamide

The pyrazolone above (6.9 g) was dissolved in phosphorous oxychloride (30 ml) and the mixture boiled under reflux for 2 hrs. The mixture was cooled and poured into icewater. The product was extracted with chloroform (3 × 50 and the combined extracts were washed with water, dried and evaporated. After crystallisation of the crude product from ethanol, 5-chloro-1,3-dimethyl-N-phenyl-4-pyrazolecarboxamide (3.9 g, 52%) was obtained as colourless needles, m.p. 157–159° C.

5-chloro-N-(3-chlorophenyl)-1,3-dimethyl-4-pyrazolecarboxamide was similarly prepared in 67% yield. It crystallised from ethanol as colourless crystals, m.p. 161–162° C.

(d) 1,3-dimethyl-N-phenyl-4-pyrazolecarboxamide 5-chloro-1,3-dimethyl-N-phenyl-4-pyrazolecarboxamide (2.7 g) was dissolved in ethanol (100 ml) and anhydrous sodium acetate (2 g) added. The mixture was hydrogenated at room temperature and 2 atmospheres pressure using palladium on carbon catalyst. On completion of the reaction, the catalyst was removed by filtration through celite and the filtrate evaporated in vacuo. Water (50 ml) was added and the product extracted with chloroform (3 × 25 ml). The combined extracts were washed with water, dried and evaporated. The product was crystallised from ethanol and 1,3-dimethyl-N-phenyl-4-pyrazolecarboxamide (2 g, 96%) was obtained as colourless needles, m.p. 91–92° C.

EXAMPLE 7

The compounds of this invention were tested in vitro against a wide variety of fungal diseases of plants. Inhibition of spore germination and mycelial were tested by the standard methods known in the art and the results are given in Table V below wherein the codes for the fungi tested have the following meanings:

Sn = *Septoria nodorum*
Uf = *Uromyces viciae-fabae*
Cc = *Cladosporium cucumerinum*
Pr = *Puccinia recondita*
Rs = *Rhizoctonia solani*
Un = *Ustilago nuda*
Tf = *Tilletia foetida*
Mf = *Monolinia fructicola*
Pc = *Phytophthora cinnamomi*
Gg = *Gauemannomyces graminis*

TABLE V
INHIBITION OF SPORE GERMINATION AND MYCELIAL GROWTH

| Compound No | Spore germination[1] | | | | | | | Mycelial growth[2] | | | |
|---|---|---|---|---|---|---|---|---|---|---|---|
| | Sn | Uf | Cc | Pr | Un | Tf | Mf | Pc | Mf | Rs | Gg |
| 3 | | ++ | | | | | | | | + | |
| 5 | | + | | | | | | | | | |
| 11 | | + | | | ++ | | | | | +++ | |
| 12 | | + | | ++ | ++ | | | | | + | |
| 13 | + | + | + | ++ | +++ | | | | | +++ | |
| 14 | | + | + | | ++ | +++ | | | | +++ | |
| 15 | | + | + | | | | | + | + | ++ | |
| 16 | | + | + | | | | | + | ++ | + | + |
| 31 | | | | | | ++ | | | | + | |
| 32 | | | | | | | | | | + | |
| 33 | | | | | +++ | | | | | + | + |
| 34 | | | | | | ++ | ++ | | + | + | + |
| 35 | | | | | | | | | | + | + |

[1]Spore germination
+++ >50% inhibition of germination at 4 ppm
++ >50% inhibition of germination at 20 ppm
+ >50% inhibition of germination at 100 ppm
[2]Mycelial growth
+++ >50% of control growth at 3 ppm
++ >50% of control growth at 10 ppm
+ >50% of control growth at 30 ppm

EXAMPLE 8

The compound of this invention were tested in vivo against *Puccinia recondita* (wheat), *Uromyces viciae-fabae* (broad beans) and *Rhizoctonia solani* (cotton). The results are shown in Table VI.

TABLE VI
SYSTEMIC AND PROTECTANT ACTIVITY IN VIVO

| Compound No | P. recondita[1] Wheat-systemic | U. viciae-fabae[2] Broad bean-protectant | R. solani[3] cotton |
|---|---|---|---|
| 3 | | | + |
| 4 | + | | |
| 5 | ++ | | |
| 6 | + | | |
| 11 | + | +++* | ++ |
| 12 | + | ++* | +++ |
| 13 | +++ | ++* | +++ |
| 14 | +++ | +++ | + |
| 17 | + | +++ | |
| 26 | | | ++ |
| 33 | | | +++ |
| 34 | | | + |
| 35 | | | + |

[1]The compound was applied as a drench to wheat seedlings grown in compost (80 c.c. pots) prior to inoculation with *P. recondita*
+++ = complete control of infection at the rate of 1 mg/pot
++ = at the rate of 2 mg/pot
+ = at the rate of 4 mg/pot
[2]The compound was applied as a protective spray to broad bean seedlings prior to inoculation with spores of *U. viciae-fabae*
+++ = infection less than 25% of control at 10 ppm
++ = infection less than 25% of control at 25 ppm
+ = infection less than 25% of control at 100 ppm
*These compounds eradicate *U. violae-fabae* when sprayed (1000 ppm) onto broad bean seedlings 48 hr after inoculation.
[3]The compound was applied to the soil pre-emergent. After emergence, the cotton seedlings were inoculated with *R. solani*
+++ = complete protection from infection at a rate of 2 Kg/ha
++ = complete protection from infection at a rate of 8 Kg/ha
+ = complete protection from infection at a rate of 16 Kg/ha

EXAMPLE 9

Certain of the compounds of this invention were tested in an in vivo glass-house trial against *Tilletia foetida* (wheat bunt).

In this test wheat seeds were inoculated with spores of *T. foetida* at 0.5%. The seeds were then treated with the test compound and incubated for 3 weeks at 10° C. The seeds were then potted into 15 cm pots, allowed to grow and the plants assessed for disease. The results are shown in Table VII.

TABLE VII
IN VIVO GLASSHOUSE TRIAL AGAINST TILLETIA FOETIDA

| Compound No | Compound concentration (ppm) | Percentage Disease |
|---|---|---|
| Control | — | 100 |
| 11 | 250 | 0 |
| 11 | 500 | 0 |
| 13 | 250 | 0 |
| 13 | 500 | 0 |
| 14 | 250 | 0 |
| 14 | 500 | 0 |
| Carboxin | 250 | 0 |
| Carboxin | 500 | 0 |
| Control | — | 75.8 |
| 33 | 125 | 0 |
| 33 | 250 | 0 |
| Fenaminosulf | 100 | 4 |

EXAMPLE 10

The compounds and compositions of the invention were tested against a variety of fungal diseases of plants. In one test (combined spray/root drench) the foliage of the plants was sprayed with a solution of the test compound and also the soil in which the plants were growing was drenched with another solution of the test compound. Both the solution used for spraying and the soil drench solution contained 100 parts per million (ppm) of the test compound.

In another test (root drench) the soil in which the plants were growing was drenched with a solution containing 250 ppm of the test compound.

The plants were infected with the disease it was desired to control before or after application of the chemical and after a period of days, depending on the particular disease, the extent of the disease was visually assessed. The results are given in Table VIII below in the form of a grading as follows:

| Grading | Percentage Amount of Disease |
|---|---|
| 0 | 61 to 100 |
| 1 | 26 to 60 |
| 2 | 6 to 25 |
| 3 | 0 to 5 |
| 4 | 0 |

The codes for the fungal disease under test are as follows:

Pr = *Puccinia recondita*
Pi = *Phytophthora infestans*
Xo = *Xanthomonas oryzae*
Po = *Piricularia oryzae*
Rs = *Rhizoctonia solani*

Table VIII
CONTROL OF PLANT FUNGAL DISEASE BY COMBINED SPRAY-ROOT DRENCH AND BY ROOT DRENCH

| Compound No | Combined Spray/Root Drench (100 ppm) | | | | Root Drench (250 ppm) |
|---|---|---|---|---|---|
| | Pr | Pi | Xo | Po | Rs |
| 11 | 4 | | 3 | | 2 |
| 13 | 4 | 2 | 3 | 1-2 | 1-2 |
| 15 | 3 | | | | |
| 30 | 4 | 2 | | 3 | 3 |
| 28 | 3 | 1-2 | | 1-3 | 2 |

We claim:

1. A process of combatting undesired fungal infestations in plants which process comprises applying to said plants, to the locus of said plants or to plant seeds prior to sowing, a fungicidally effective amount of a compound of the formula

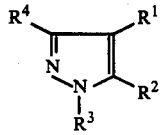

wherein either $R^1$ or $R^2$ is the group —$CONHR^5$ in which $R^5$ is phenyl or phenyl substituted with one, two or three substituents which are independently chosen from the group consisting of alkyl, alkoxy, halogen, trifluoromethyl, nitro and cyano; $R^3$ is chosen from the group consisting of hydrogen, alkyl, hydrofyolkyl, phenyl and —$CH_2COOR^6$ wherein $R^6$ is alkyl; $R^4$ and $R^1$ or $R^2$, whichever is not —$CONHR^5$, are chosen from the group consisting of hydrogen, halogen and alkyl provided that when $R^1$ is —$CONHR^5$, then $R^2$ and $R^4$ are not both hydrogen, and when $R^2$ is —$CONHR^5$ then $R^1$ and $R^3$ are not both hydrogen.

2. A process according to claim 1 wherein the active ingredient is a compound of the indicated formula in which: $R^1$ or $R^2$ is the group —$CONHR^5$ in which $R^5$ is phenyl or phenyl substituted with one or two substituents independently chosen from the group consisting of methyl, ethoxy, halogen, nitro and trifluoromethyl; when $R^1$ is the group —$CONHR^5$, then $R^3$ is chosen from the group consisting of hydrogen, methyl, hydroxyethyl, phenyl and $CH_2COOC_2H_5$, $R^4$ is methyl and $R^2$ is hydrogen, methyl or halogen; and when $R^2$ is the group —$CoNHR^5$, then $R^3$ and $R^4$ are methyl and $R^1$ is hydrogen.

3. A process according to claim 1 wherein $R^1$ is —$CONHR^5$, $R^3$ is hydrogen, methyl or phenyl, $R^4$ is methyl or halogen.

4. A process according to claim 2 wherein $R^2$ is —$CONHR^5$ in which $R^5$ is phenyl or phenyl substituted with methyl or halogen, $R^1$ is hydrogen and $R^3$ and $R^4$ are both methyl.

5. A process according to claim 3 wherein $R^2$ is methyl or chlorine, $R^3$ is hydrogen, methyl or phenyl, $R^4$ is methyl or chlorine and $R^5$ is phenyl or phenyl substituted with one or two substituents chosen from the group consisting of methyl, chlorine, ethoxy, nitro and trifluoromethyl.

6. A process according to claim 4 wherein $R^1$ is hydrogen, $R^3$ is methyl, $R^4$ is methyl and $R^5$ is phenyl or phenyl substituted with methyl or chlorine.

7. A process according to claim 1 wherein the active ingredient is 1,3,5-trimethyl-N-(m-tolyl)-4-pyrazolecarboxamide.

8. A process according to claim 1 wherein the active ingredient is N-(3-chlorophenyl)-1,3,5-trimethyl-4-pyrazolecarboxamide.

9. A process according to claim 1 wherein the active ingredient is 1,3-dimethyl-N-(o-tolyl)-5-pyrazolecarboxamide.

10. A process according to claim 1 wherein the active ingredient is 5-chloro-1,3-dimethyl-N-phenyl-4-pyrazolecarboxamide.

11. A composition for use in combatting undesired fungal infestations in plants which comprises as active ingredient from 0.0001 to 1% by weight of a compound of the formula

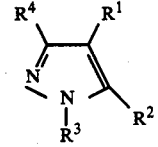

wherein either $R^1$ or $R^2$ is —$CONHR^5$ in which $R^5$ is phenyl or phenyl substituted with one, two or three substituents, which may be the same or different, chosen from the group consisting of alkyl, alkoxy, halogen, trifluoromethyl, nitro and cyano; $R^3$ is chosen from the group consisting of hydrogen, alkyl, hydroxyalkyl, phenyl and —$CH_2COOR^6$ wherein $R^6$ is alkyl; $R^4$ and $R^1$ or $R^2$, whichever is not —$CONHR^5$, may be the same or different and are chosen from the group consisting of hydrogen, halogen and alkyl; provided that when $R^1$ is —$CONHR^5$, then $R^2$ and $R^4$ are not both hydrogen, when $R^1$ is —$CONHR^5$ and $R^2$, $R^3$ and $R^4$ are each methyl, then $R^5$ is not unsubstituted phenyl, and when $R^2$ is the —$CONHR^5$, then $R^1$ and $R^3$ are not both hydrogen; and an inert carrier material for said compound.

12. A composition according to claim 11 wherein the active ingredient is a compound of the indicated formula in which $R^1$ or $R^2$ is —$CONHR^5$ in which $R^5$ is phenyl or phenyl substituted with one or two substituents independently chosen from the group consisting of methyl, ethoxy, halogen, nitro and trifluoromethyl; when $R^1$ is the group —$CONHR^5$, then $R^3$ is chosen from the group consisting of hydrogen, methyl, hydroxyethyl, phenyl and $CH_2COOC_2H_5$, $R^4$ is methyl and $R^2$ is hydrogen, methyl or halogen and; when $R^2$ is —$CONHR^5$, then $R^3$ and $R^4$ are methyl and $R^1$ is hydrogen.

13. A composition according to claim 12 wherein the active ingredient is 1,3,5-trimethyl-N-(m-tolyl)-4-pyrazolecarboxamide.

14. A composition according to claim 12 wherein the active ingredient is N-(3-chlorophenyl)-1,3,5-trimethyl-4-pyrazolecarboxamide.

15. A composition according to claim 12 wherein the active ingredient is 1,3-dimethyl-N-(o-tolyl)-5-pyrazolecarboxamide.

16. A composition according to claim 12 wherein the active ingredient is 5-chloro-1,3-dimethyl-N-phenyl-4-pyrazolecarboxamide.

* * * * *